(12) United States Patent
Shiakolas et al.

(10) Patent No.: US 11,529,055 B2
(45) Date of Patent: Dec. 20, 2022

(54) ARTICULABLE DEVICES FOR IN VIVO TISSUE EVALUATION

(71) Applicant: Board of Regents, The University of Texas System, Austin, TX (US)

(72) Inventors: Panayiotis S. Shiakolas, Austin, TX (US); Shashank Kumat, Austin, TX (US); Samson Abimbola Adejokun, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 50 days.

(21) Appl. No.: 17/259,152

(22) PCT Filed: Jul. 10, 2019

(86) PCT No.: PCT/US2019/041261
§ 371 (c)(1),
(2) Date: Jan. 8, 2021

(87) PCT Pub. No.: WO2020/014401
PCT Pub. Date: Jan. 16, 2020

(65) Prior Publication Data
US 2021/0267456 A1   Sep. 2, 2021

Related U.S. Application Data

(60) Provisional application No. 62/696,157, filed on Jul. 10, 2018.

(51) Int. Cl.
*A61B 5/00* (2006.01)
*A61B 5/20* (2006.01)

(52) U.S. Cl.
CPC .............. *A61B 5/0053* (2013.01); *A61B 5/20* (2013.01); *A61B 5/6874* (2013.01); *A61B 2562/0261* (2013.01)

(58) Field of Classification Search
CPC ....... A61B 5/0053; A61B 5/20; A61B 5/6874; A61B 5/6852; A61B 2562/0261; A61B 2562/0247
See application file for complete search history.

(56) References Cited

U.S. PATENT DOCUMENTS

| | | | |
|---|---|---|---|
| 2011/0092955 A1* | 4/2011 | Purdy | A61B 5/0261 604/523 |
| 2013/0123783 A1* | 5/2013 | Marczyk | A61B 18/1445 606/1 |
| 2017/0296178 A1* | 10/2017 | Miller | A61B 5/0053 |
| 2019/0247045 A1* | 8/2019 | Park | A61B 17/072 |
| 2020/0038121 A1* | 2/2020 | Yang | A61B 18/1445 |
| 2021/0267709 A1* | 9/2021 | Rauter | A61B 1/05 |

* cited by examiner

*Primary Examiner* — Sean P Dougherty
*Assistant Examiner* — Alexander H Connor
(74) *Attorney, Agent, or Firm* — Thomas | Horstemeyer, LLP

(57) ABSTRACT

In one embodiment, a device for in vivo tissue evaluation includes an elongated manipulator including an elongated proximal tube and an articulable distal portion, and a sensor provided at a distal end of the articulable distal portion, the sensor including a sensor head configured to be pressed against tissue and measure a reaction force of the tissue.

8 Claims, 11 Drawing Sheets

ARTICULABLE DEVICES FOR IN VIVO TISSUE EVALUATION

CROSS-REFERENCE TO RELATED APPLICATION

This application is the 35 U.S.C. § 371 national stage application of PCT Application No. PCT/US19/41261, filed Jul. 10, 2019, where the PCT claims priority to and the benefit of U.S. Provisional Application Ser. No. 62/696,157, filed Jul. 10, 2018, all of which is hereby incorporated by reference herein in their entireties.

BACKGROUND

The human bladder is a vital organ of the excretory system. The biomechanical properties of the tissues of the bladder can be indicative of the bladder's health. For example, it has been observed that, while healthy bladders are relatively stiff, cancerous bladders can be relatively elastic. Currently, the most common way to assess such properties of the bladder's tissues is for a physician to simply press upon the patient's lower abdomen to obtain an idea of the state of the bladder. As such a procedure only provides a subjective impression as to the properties of the bladder, it would be preferable to be able to directly access the tissues of the bladder in vivo for the purpose of directly measuring one or more biomechanical properties of those tissues as a part of an evaluation of the bladder's health.

Current technologies used to access the bladder include both rigid and flexible cystoscopes. A cystoscope is a device designed to be passed through the urethra and into the bladder for the purpose of visually inspecting the urethra and the bladder. While such a device could potentially be used to measure biomechanical properties of the tissues of the bladder, the average outer diameter of a cystoscope is approximately 7 mm. As this is a relatively large dimension as compared to the inner diameter of the urethra, which is typically 3 to 4 mm, general anesthesia is needed to numb the urethra during a cystoscopy. Understandably, it would be desirable to have a device that could be used to access the bladder via the urethra that is significantly smaller than conventional cystoscopes so as to reduce patient discomfort and other complications. In addition, it would be desirable for such a device to have a sensor that could be used to measure one or more biomechanical properties of the tissues of the bladder.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
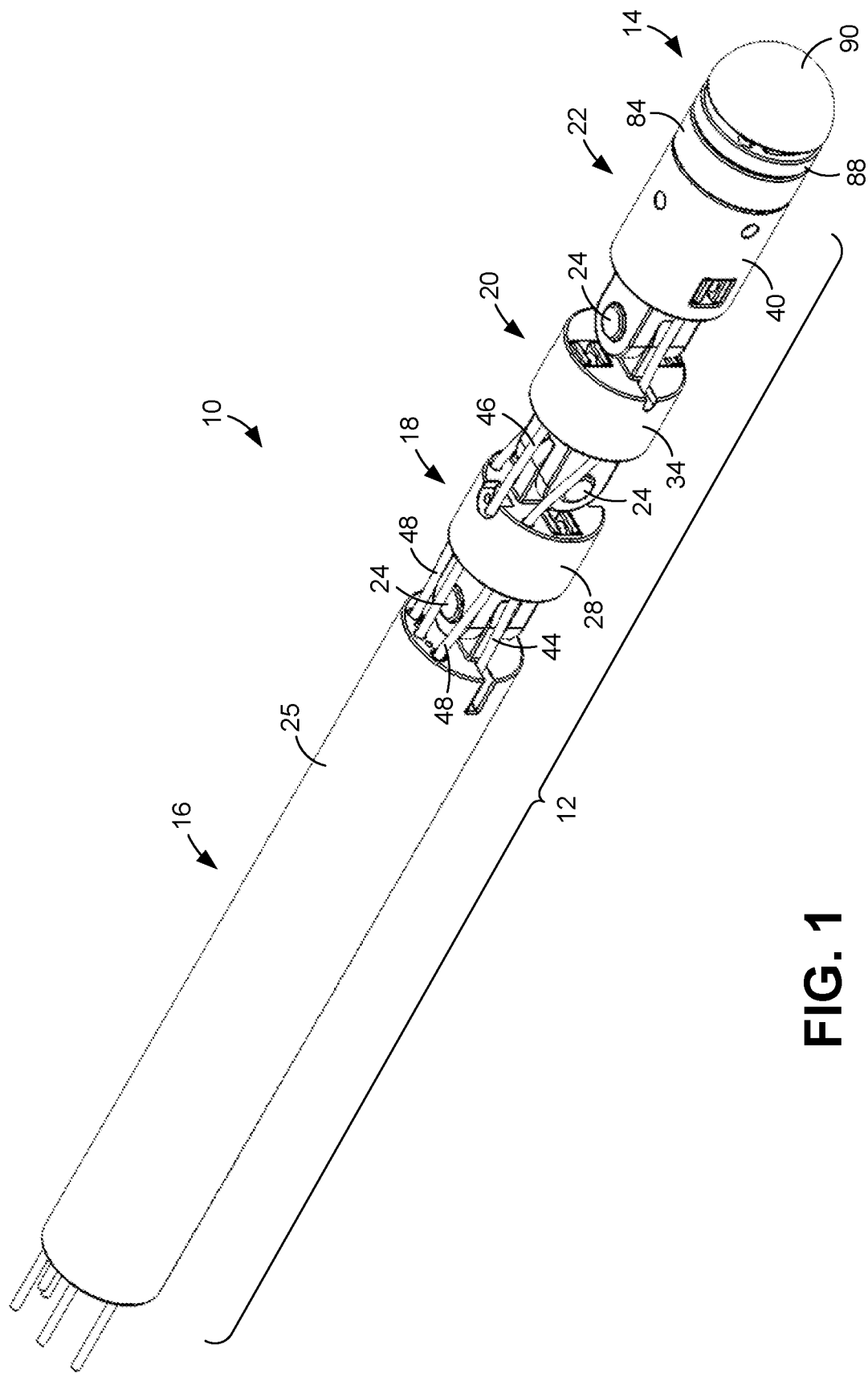
FIG. 1 is a perspective view of a first embodiment of an articulable device for in vivo tissue evaluation.

As described above, it would be desirable to have a device that can be used to access the bladder via the urethra that is significantly smaller than conventional cystoscopes for the purpose of measuring one or more biomechanical properties of the tissues of the bladder. Disclosed herein are articulable devices for in vivo tissue evaluation having relatively small outer dimensions that can be passed through the urethra and into the bladder. In some embodiments, the devices comprise a manipulator having a force sensor that can be pressed against tissues within the bladder to measure a reaction force of the tissues for purposes of assessing the health of the bladder. In some embodiments, the devices comprise multiple articulable links that can be moved relative to each other so that the device can be articulated within the bladder to access all areas of the bladder, including the trigone.

In the following disclosure, various specific embodiments are described. It is to be understood that those embodiments are example implementations of the disclosed inventions and that alternative embodiments are possible. Such alternative embodiments include hybrid embodiments that incorporate features from different disclosed embodiments. All such embodiments are intended to fall within the scope of this disclosure.

FIGS. 1-8 illustrate a first embodiment of an articulable device 10 for in vivo tissue evaluation that is configured to pass through the urethra and into the bladder. Beginning with FIG. 1, the device 10 generally comprises an elongated manipulator 12 having a force sensor 14 provided at its distal end. As is apparent from FIG. 1, the manipulator 12 generally comprises an elongated proximal tube 16 and an articulable distal portion that includes a first articulable intermediate link 18, a second articulable intermediate link 20, and an articulable end link 22. In the illustrated embodiment, the tube 16 and the links 18-22 are generally cylindrical and are made of a suitable rigid, biocompatible material, such as stainless steel or a suitable polymer material. The tube 16 and the links 18-22 each have a relatively small outer dimension (e.g., diameter) for easier passage through the urethra. In some embodiments, this tube 16 and links 18-22 have an outer diameter that is no greater than 3 mm. Although not shown in FIG. 1, the device 10 can further include an outer guide tube that can be inserted through the urethra that acts as a guide through which the manipulator 12 can be passed. Such a guide tube can also be generally cylindrical and can have an outer dimension (e.g., diameter) no greater than 3.5 mm.

The proximal tube 16 and articulable links 18-22 are all pivotally connected to each other. More particularly, the first intermediate link 18 is pivotally connected to the tube 16, the second intermediate link 20 is pivotally connected to the first intermediate link, and the end link 22 is pivotally connected to the second intermediate link. The nature of those connections is more clearly apparent from FIG. 2, which is an exploded view of the assembled device 10 shown in FIG. 1.

Figure 2:
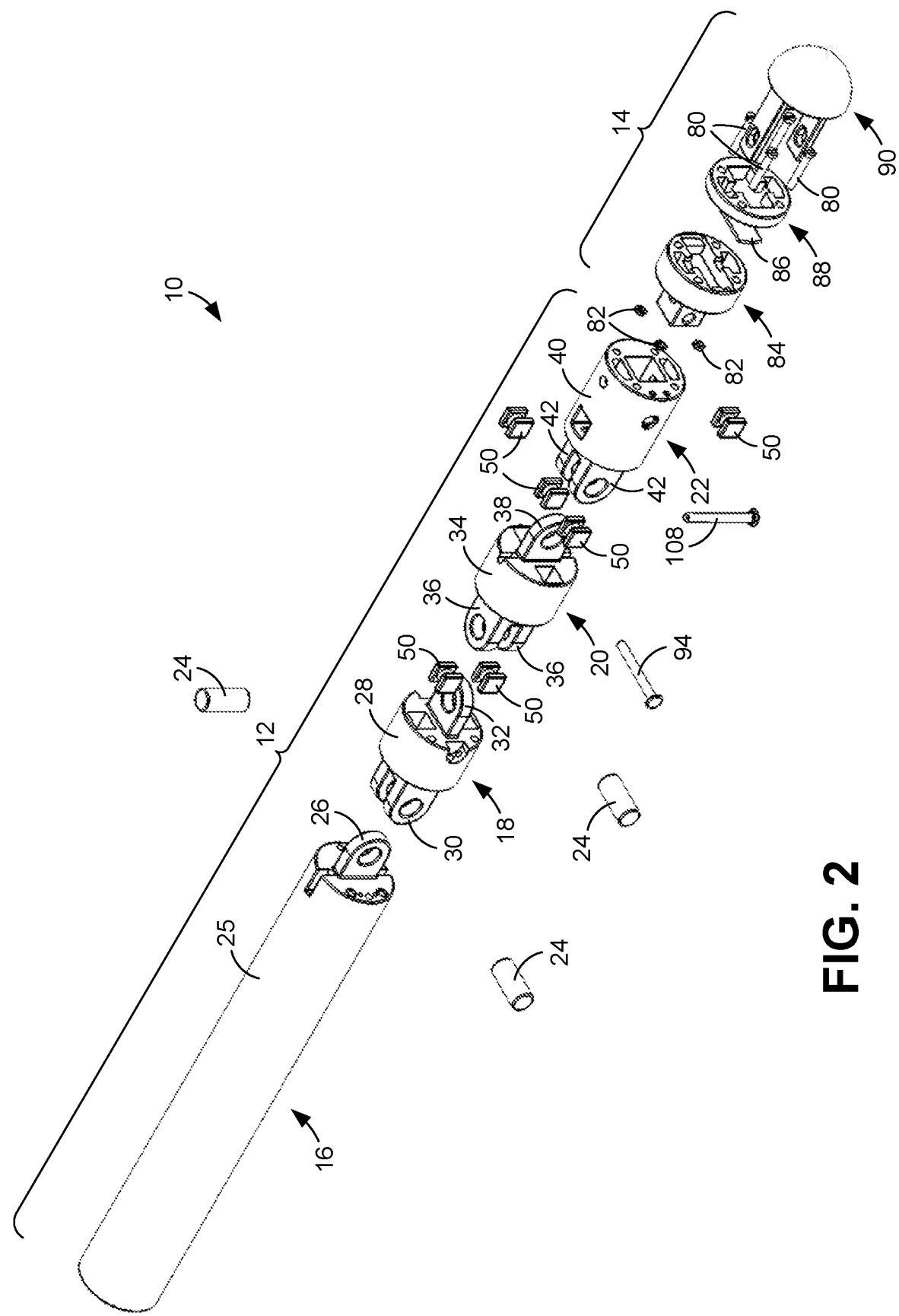
FIG. 2 is an exploded perspective view of the device of FIG. 1.
Figure 3A:
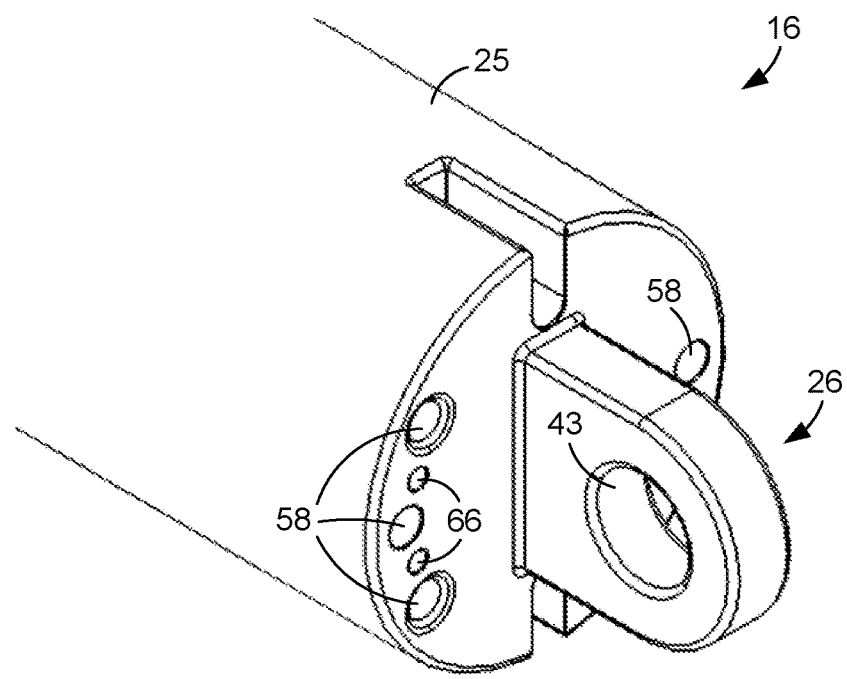
FIG. 3A is a partial perspective view of an embodiment of a proximal tube of the device of FIG. 1.
Figure 3B:
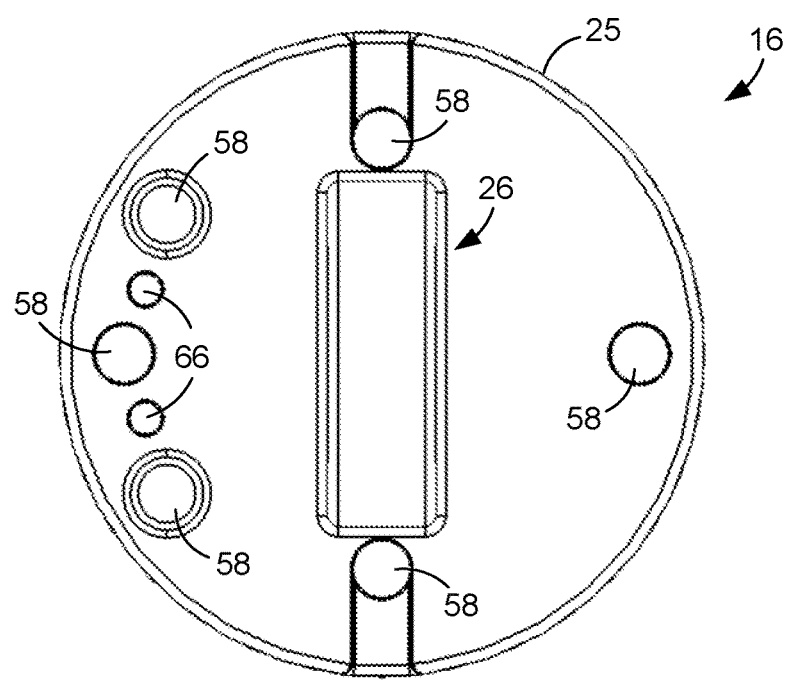
FIG. 3B is an end view of the proximal tube of FIG. 3A.
Figure 4A:
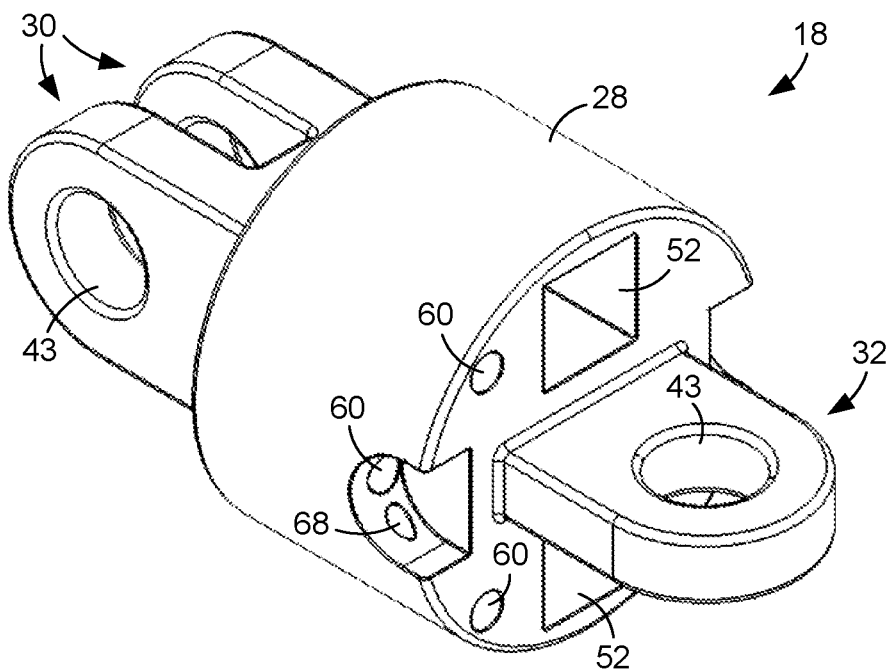
FIG. 4A is a perspective view of an embodiment of a first intermediate link of the device of FIG. 1.
Figure 4B:
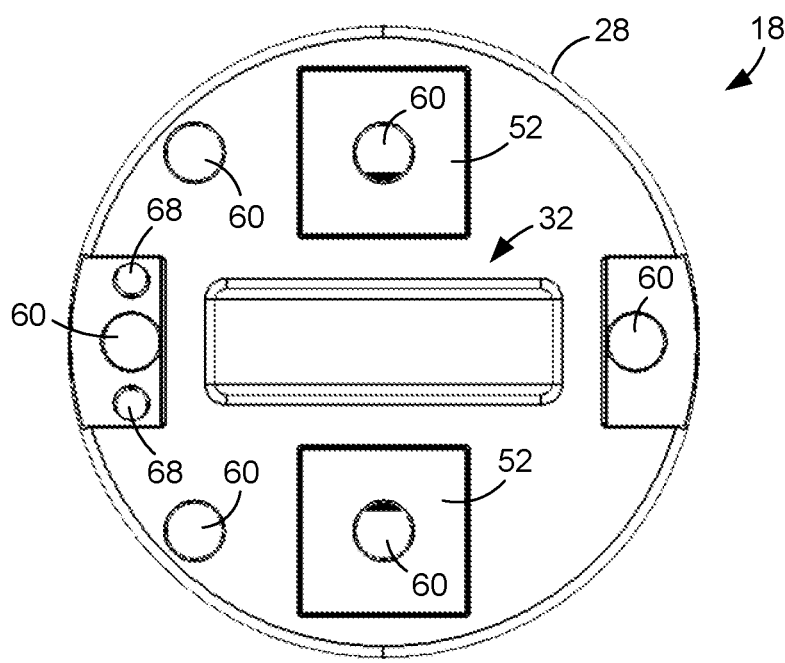
FIG. 4B is an end view of the first intermediate link of FIG. 4A.
Figure 5A:
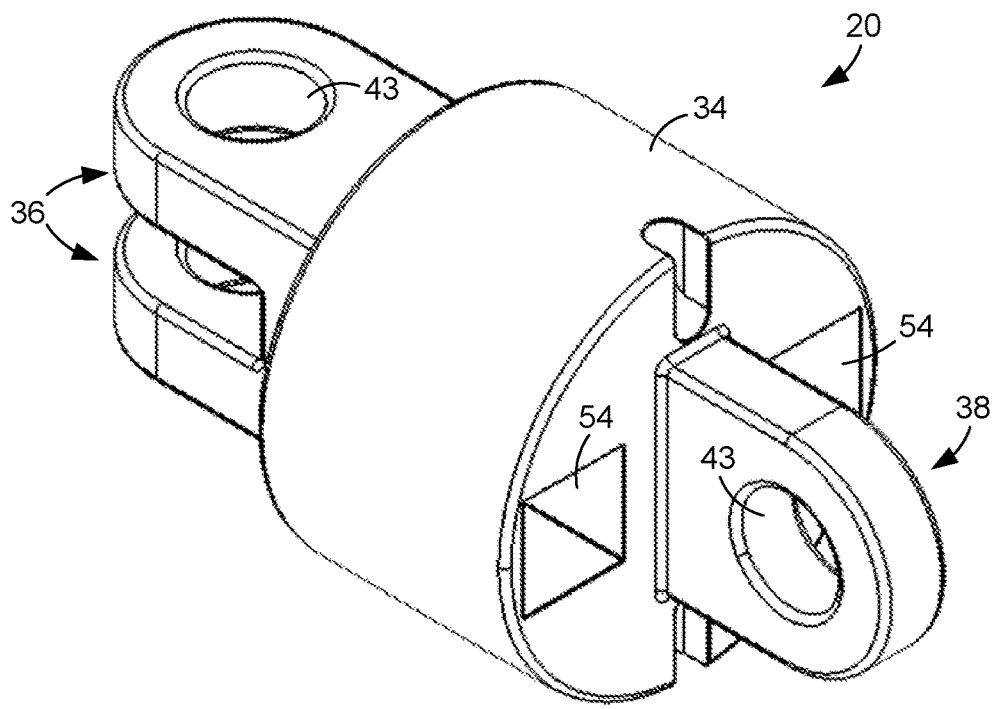
FIG. 5A is a perspective view of an embodiment of a second intermediate link of the device of FIG. 1.
Figure 5B:
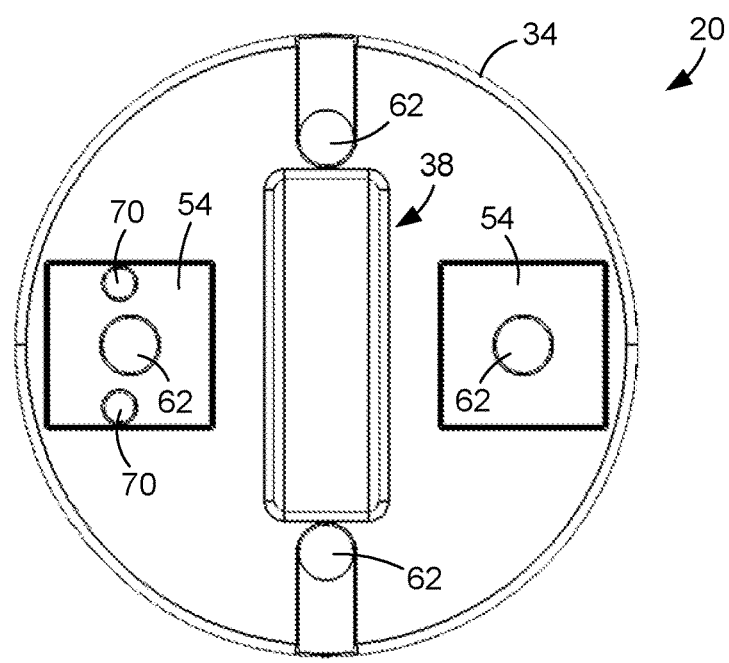
FIG. 5B is an end view of the second intermediate link of FIG. 5A.

As shown in FIG. 2, the tube 16 and each link 18-22 includes mounting flanges through which pivot pins 24 are passed to connect the components. With reference to FIGS. 3A and 3B, the tube 16 includes a body 25 from which a single mounting flange 26 extends. With reference to FIGS. 4A and 4B, the first intermediate link 18 includes a body 28 from which extend two proximal mounting flanges 30 and a distal mounting flange 32. With reference to FIGS. 5A and 5B, the second intermediate link 20 includes a body 34 from which extend two proximal mounting flanges 36 and a distal mounting flange 38. Finally, with reference to FIGS. 6A and 6B, the end link 22 includes a body 40 from which extend two proximal mounting flanges 42. Each of these flanges includes an opening 43 through which a pivot pin 24 can be inserted. With reference back to FIG. 1, when the tube 16 and links 18-22 are connected using the pivot pins 24 and the various mounting flanges, the links can pivot about the pivot pins (pivot axes) relative to the tube and/or other links. As is apparent from FIG. 1, each pivot pin 24 can be orthogonally arranged relative to its adjacent pivot pin(s) so that the links can be articulated in different orthogonal planes.

With such pivotal connection, the articulable links 18-22 can be pivoted (i.e., articulated) to position the sensor 14 in any desired location and orientation when within the bladder, including the trigone. Control over this articulation is made possible by the provision of multiple tendons that extend along the length of the manipulator 12 and that attach to the various links 18-22. In the illustrated embodiment, three pairs of tendons are provided, with one pair being attached to each link 18-22. These tendons include a first pair of tendons 44 that attach to and terminate at the first intermediate link 18, a second pair of tendons 46 that attach to and terminate at the second intermediate link 20, and a third pair of tendons 48 that attach to and terminate at the end link 22. These tendons 44-48 can be more clearly viewed in FIG. 7, which shows the manipulator 12 with the links 18-22 hidden. As can be appreciated from this figure, the tendons associated with each link 18-22 are positioned on opposite sides of the manipulator 12 so that they can be alternatively pulled to cause the associated link to pivot to the side of the link to which the tendon is attached.

Figure 6A:
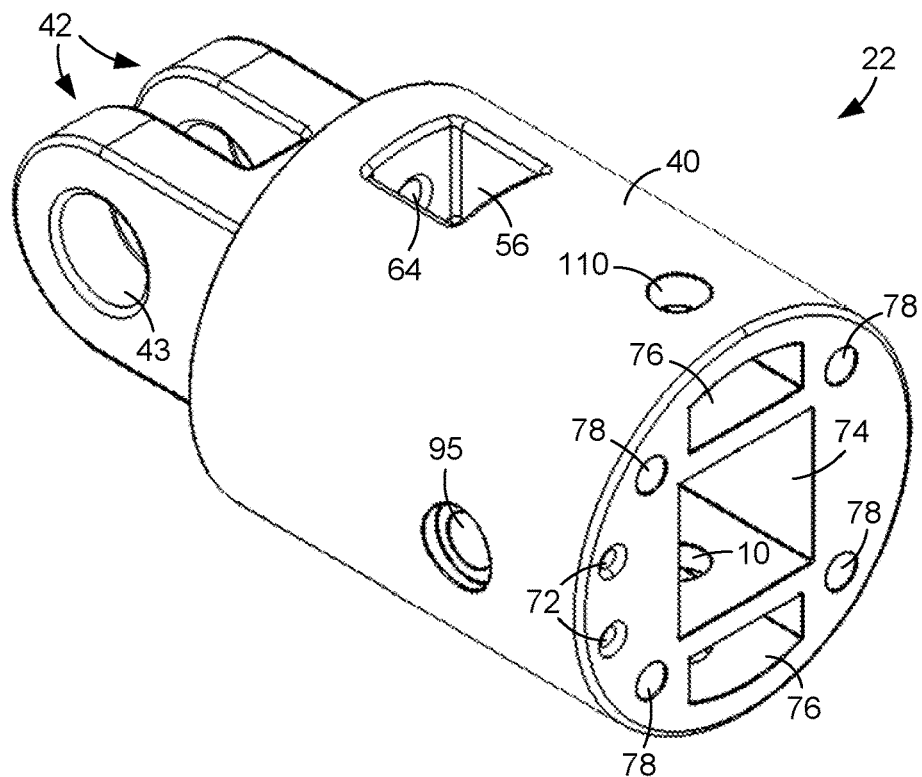
FIG. 6A is a perspective view of an embodiment of an end link of the device of FIG. 1.
Figure 7:
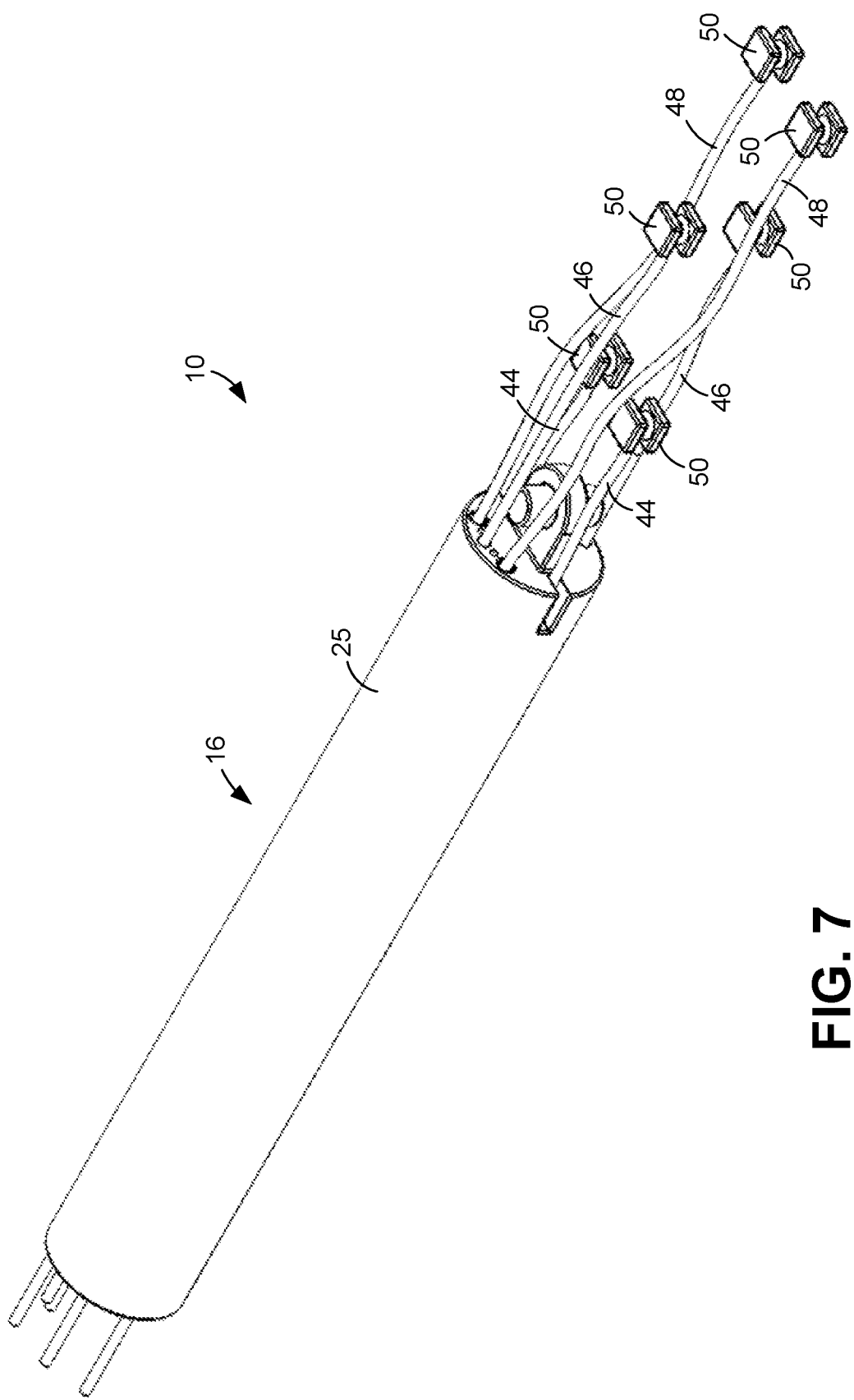
FIG. 7 is a perspective view of the device of FIG. 1 with the links removed so as to show tendons of the device more clearly.

With further reference to FIG. 7, each tendon 44-48 is connected to an attachment element 50 that is provided to secure the tendon to its link. In the illustrated embodiment, each attachment element 50 is configured as an I-beam element having a central shaft that is terminated on each end by an end flange that is generally orthogonal to the longitudinal axis of the shaft. The distal end of each tendon 44-48 can be wrapped around a shaft of an attachment element 50, which can then be press-fit into one of the articulable links 18-22 to secure the tendon to its associated link. In particular, each link 18-22 includes a cavity that is configured to receive an attachment element 50. For example, the first intermediate link 18 includes two cavities 52 (see FIGS. 4A and 4B), the second intermediate link 20 includes two cavities 54 (see FIGS. 5A and 5B), and the end link 22 includes two cavities 56 (see FIG. 6A, only one cavity visible in the figure).

The tendons 44-48 reach these cavities 52-56 through tendon passages that are formed in the proximal tube 16 and the articulable links 18-22. With reference to FIGS. 3A and 3B, the tube 16 includes six tendon passages 58. With reference to FIGS. 4A and 4B, the first intermediate link 18 also includes six tendon passages 60. With reference to FIGS. 5A and 5B, the second intermediate link 20 includes four tendon passages 62. With reference to FIG. 6A, the end link 22 includes two tendon passages 64 (only one passage visible in the figure). In addition to the tendon passages 58-64, the tube 16 and links 18-22 also include conductor passages that enable electrical conductors, such as insulated metal wires, to extend through the manipulator 12 to the sensor 14. With reference to FIGS. 3A and 3B, the tube 16 includes two conductor passages 66. With reference to FIGS. 4A and 4B, the first intermediate link 18 includes two conductor passages 68. With reference to FIGS. 5A and 5B, the second intermediate link 20 includes two conductor passages 70. With reference to FIG. 6A, the end link 22 includes two conductor passages 72.

Figure 6B:
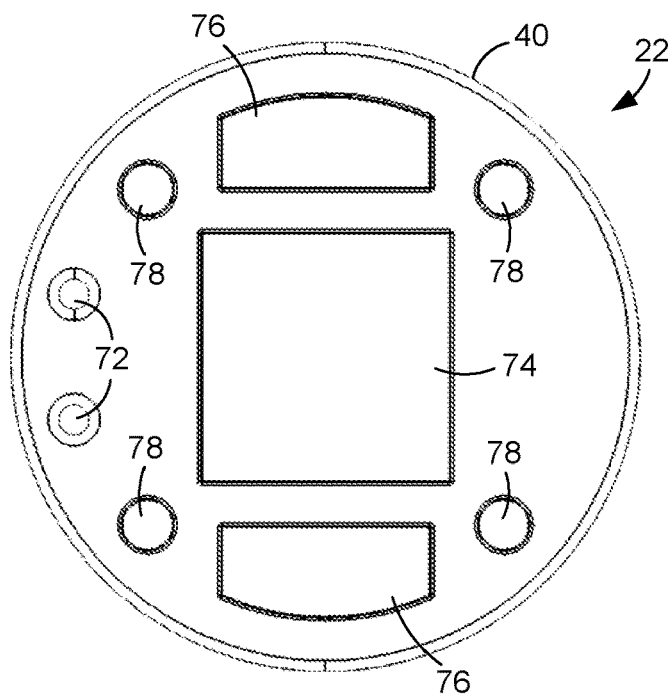
FIG. 6B is an end view of the end link of FIG. 6A.
Figure 8:
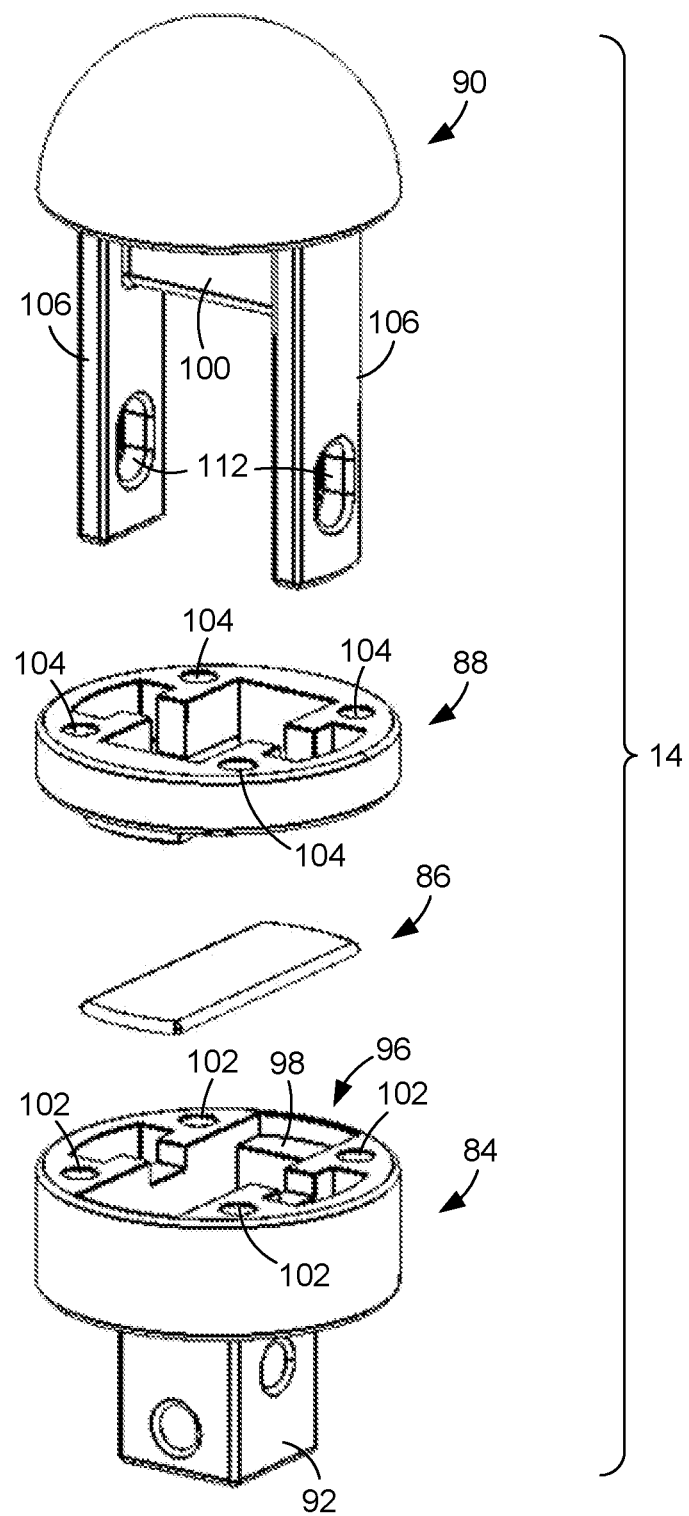
FIG. 8 is an exploded perspective view of an embodiment of a sensor of the device of FIG. 1.

Referring next to FIGS. 6A and 6B, the end link 22 also includes features that are configured to accommodate the sensor 14. These features include a central cavity 74 and two lateral cavities 76 that are configured to receive components of the sensor 14, and fastener openings 78 that are configured to receive threaded fasteners 80 (see FIG. 2) used to secure a beam of the sensor (discussed below) with nuts 82. FIG. 8 shows the sensor 14 in an exploded view. As illustrated in this figure, the sensor 14 comprises a sensor body 84, a sensor beam 86, a beam clamp 88, and a sensor head 90. The body 84 includes a mounting tang 92 that is configured to be received in the central cavity 74 of the end link 22 and secured with a threaded fastener 94, as well as a fastener 108 identified below (see FIG. 2), that passes through fastener openings 95 and 110. The body 84 also includes a cavity 96 that is adapted to receive the beam 86. As is apparent in FIG. 8, opposed ledges 98 are provided within the cavity 96 that are configured to support opposed ends of the beam 86 so that the central portion of the beam can be inwardly (proximally) deformed under force provided by the head 90. The beam 86 is made of a material that enables the beam to flex, such as a polymeric or stainless steel material, so that the beam will deform when a force is applied but return to its original shape once the force is removed (i.e., elastic deformation). The beam clamp 88 is configured to securely clamp the ends of the beam 86 to the ledges 98 so that the beam cannot shift during use of the device 10.

The sensor head 90 includes an inwardly (proximally) facing protrusion 100 that is configured to engage the beam 86. As can be appreciated from the figure, the protrusion 100 is transversely arranged relative to the beam 86. The beam 86 includes one or more sensing elements (not visible in the figure), such as one or more strain gauges, that are fixedly attached to the beam that can measure strain within the beam as it is deformed by the protrusion 100. Also shown in FIG. 8 are fastener openings 102 provided in the body 84 and fastener openings 104 provided in the beam clamp 88 that are configured to receive the threaded fasteners 80. Further shown in FIG. 8 are two tangs 106 that extend inwardly (proximately) from the head 90. These tangs 106 extend through the clamp 88 and into the body 84 and are retained by a further threaded fastener 108 (see FIG. 2). More particularly, the fastener 108 extends through a fastener opening 110 formed in the end link 22 and passes through elongated slots 112 formed in the tangs 106 that are configured to enable the head 90 to move along a longitudinal axis of the sensor 14 without separating from the remainder of the sensor.

During use of the device 10, the guide tube is inserted through the urethra and into the bladder. The manipulator 12 can then be passed through the guide tube and into the bladder as well. Once inside the bladder, the manipulator 12 can be linearly translated and its distal end can be articulated using the tendons 44-48 to place the sensor head 90 into direct contact with any desired tissue within the bladder, including tissue in the trigone region. In some embodiments, this placement can be performed manually using suitable manual controls (e.g., knobs, joysticks, etc.) or automatically using computer-controlled actuators. In either case, the head 90 can be used to measure one or more biomechanical properties of the tissue. In some embodiments, the head 90 can be controllably pressed against the tissue, preferably while in an orientation perpendicular to the tissue, and the reaction force of the tissue can be determined. When the head 90 is pressed against the tissue, the head is urged inward against the beam 86 so as to deform it. The strain within the beam 86 can be measured by the one or more sensor elements, which provide data (e.g., strain data) that can be used to calculate the reaction force of the tissue. Once the reaction force of the tissue is known, it can be used as a consideration in the assessment of the health of the tissue and, ultimately, the bladder.

Figure 9:
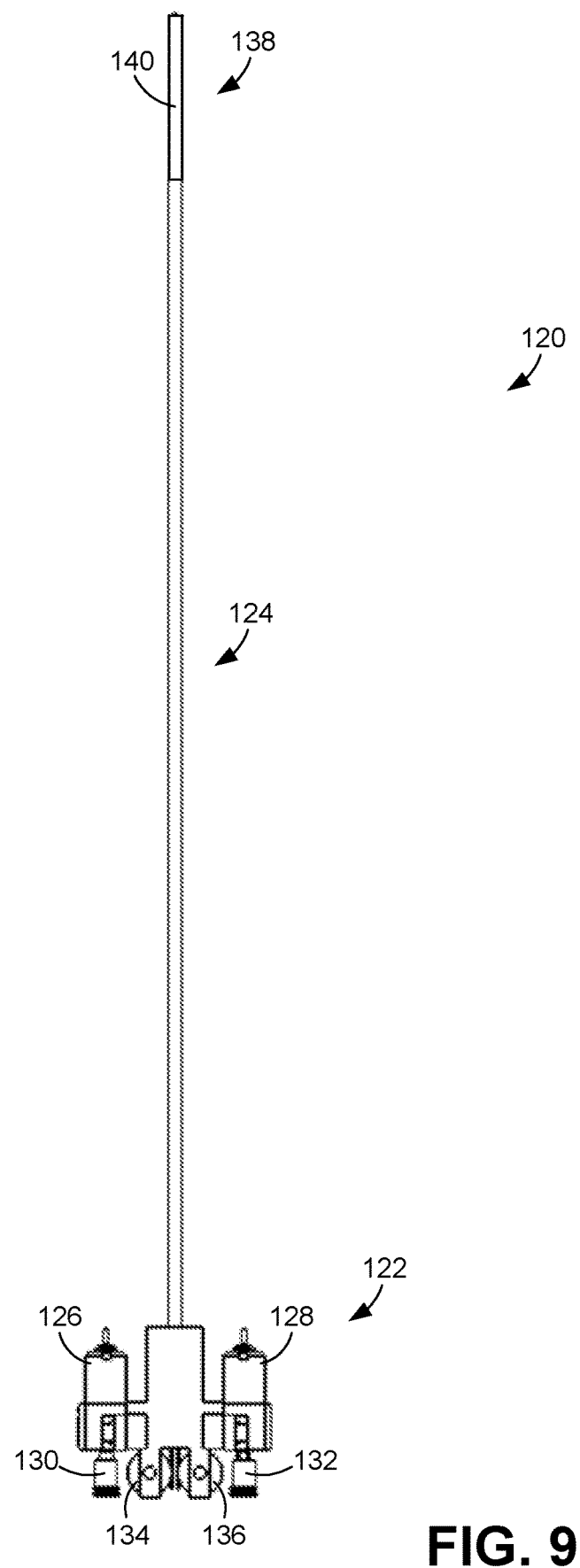
FIG. 9 is a side view of a second embodiment of an articulable device for in vivo tissue evaluation.
Figure 10:
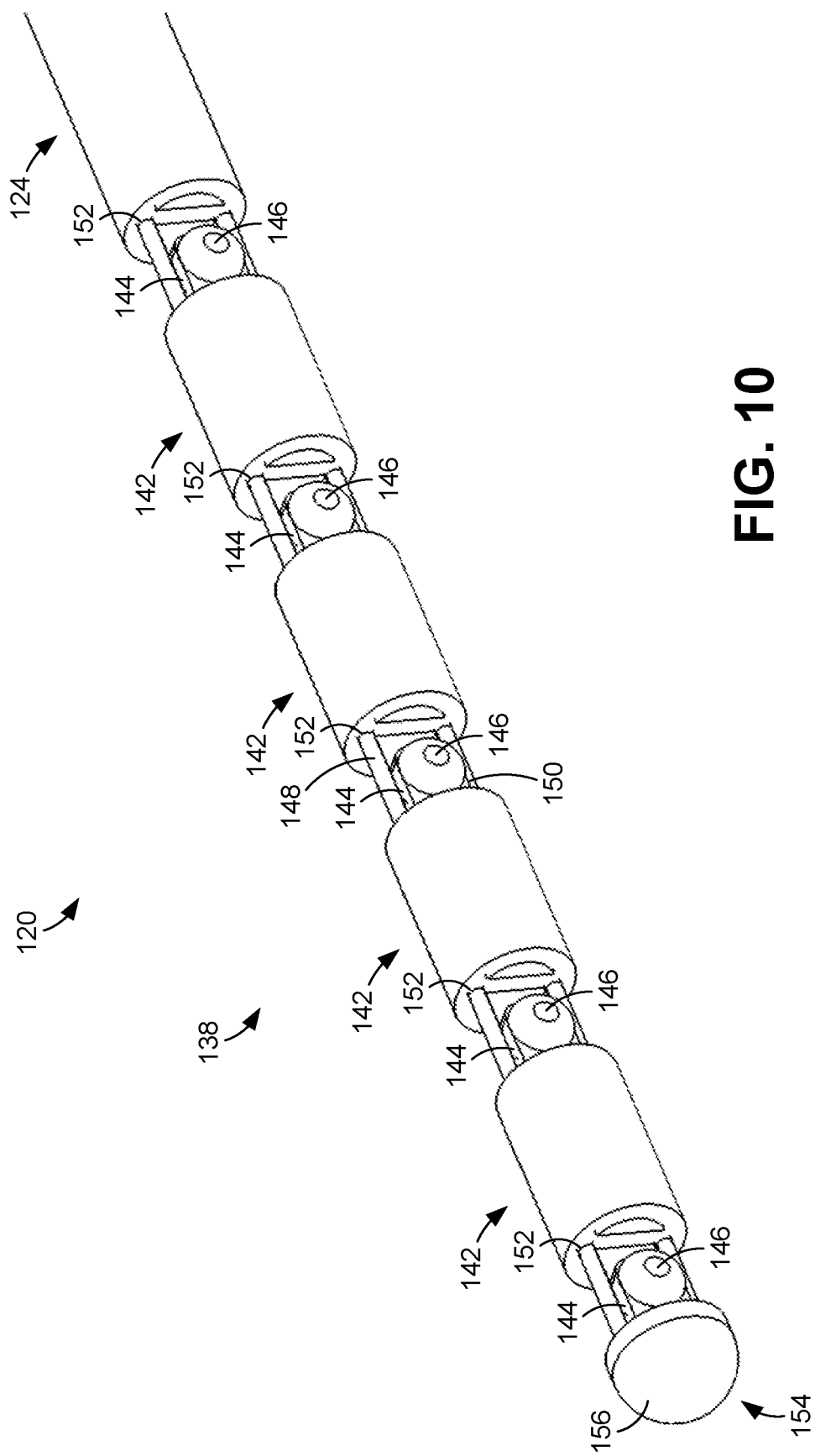
FIG. 10 is a perspective view of an embodiment of a flexible distal portion of the device of FIG. 9.
Figure 11:
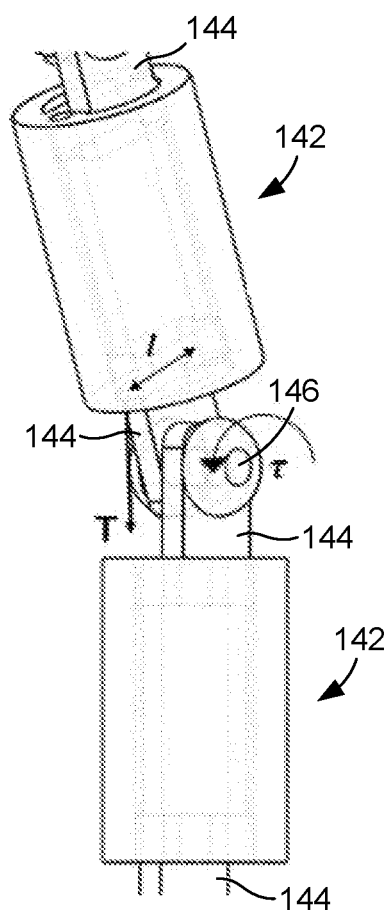
FIG. 11 is a partial perspective view of the flexible distal portion shown in FIG. 10 illustrating pivotal connection of two links of the portion.

FIGS. 9-11 illustrate another embodiment of an articulable device 120 for in vivo tissue evaluation. This device 120 can be attached to a base (not shown) that enables the device to be translated and rotated in multiple directions. For example, the device 120 can comprise a three-axis coordinate frame that enables the device to be rotated about any of the three axes independently. As shown in FIG. 9, the device 120 generally includes an actuation mechanism 122 from which extends an elongated rigid tube 124. The actuation mechanism 122 comprises left and right actuation motors 126 and 128, and left and right tendon pulleys 130 and 132 that are associated with the left and right actuation motors, respectively. In addition, the actuation mechanism 122 further comprises left and right tendon guide pulleys 134 and 136.

During operation of the device 120, the motors 126, 128 can be alternatively actuated to wind up a left tendon or a right tendon (see FIG. 10) on the tendon pulleys 130, 132 to pull an articulable distal portion 138 of the device 120 to the left or the right. As shown in FIG. 9, the distal portion 138 includes a flexible outer tube 140 that surrounds multiple articulable links, which are illustrated in FIG. 10. In some embodiments, the outer tube 140 is made of flexible material, such as silicone, and both it and the tube 124 have outer dimensions (e.g., diameters) no greater than 3 mm.

With reference to FIG. 10, illustrated in greater detail is the articulable distal portion 138 of the device 120. The flexible outer tube 140 has been removed in this figure to more clearly show the inner components of the distal portion 138. As illustrated in FIG. 10, the articulable distal portion 138 includes four articulable links 142. Each link 142 includes proximal and distal mounting flanges 144 that enable the link to be pivotally connected to the tube 124 and/or another link. As shown in FIG. 11, the mounting flanges 144 can be laterally offset relative to each other so that the mounting flanges of an adjacent link do not interfere with each other. Referring back to FIG. 10, extending through the mounting flanges 144 are pivot pins 146 that maintain the pivotal connections. Unlike the links of the first articulable device 10, the links 142 of the articulable distal portion 138 are each configured to pivot within the same plane using two tendons 148 and 150 (as opposed to separate tendon pairs for each link), which are provided on opposite sides of the distal portion 138. The tendons 148, 150 extend through tendon passages 152 formed through the tube 124 and each link 142.

Pivotally attached to the distal-most link 142 with a mounting flange 144 and a pivot pin 146 is a sensor 154, which can have a configuration similar to the sensor 14 described above. Accordingly, the sensor 154 includes a sensor head 156 that transmits forces to an internal sensing element, such as a strain gauge provided on an internal flexible beam.

The device 120 can be used in similar manner to the device 10. In particular, the articulable distal portion 138 of the device 10 can be passed through an outer guide tube positioned within the urethra to access the bladder. Once inside the bladder, the tube 124 can be actuated to extend or retract to a desired position and the distal portion 138 can be articulated using the tendons 148, 150 to place the sensor head 156 in contact and in the correct orientation with any desired tissue within the bladder. In some embodiments, this placement can be performed using the motors 126, 128 under computer control. The head 156 can be pressed against the tissue and the reaction force of the tissue can be determined. Once the reaction force of the tissue is known, it can be used as a consideration in the assessment of the health of the tissue and, ultimately, the bladder.

It is noted that, while the disclosed devices have been described herein as being used to evaluate tissues of the bladder, the devices can be used to evaluate other tissues within the body. Accordingly, the devices are not limited to any particular application.

Claimed are:

1. A device for in vivo tissue evaluation, the device comprising:
    an elongated manipulator including an elongated proximal tube and an articulable distal portion, the articulable distal portion including multiple articulable links that are pivotally connected together, the elongated manipulator further including tendons that pass through the articulable links configured to pivot the links, wherein a pair of tendons is attached to each articulable link with an attachment element that is press-fit into a cavity of the articulable link, wherein the attachment elements are I-beam elements each having a central shaft and opposed end flanges and wherein the tendons wrap around the central shafts; and
    a sensor provided at a distal end of the articulable distal portion, the sensor including a sensor head configured to be pressed against tissue and measure a reaction force of the tissue.

2. The device of claim 1, wherein the elongated manipulator is cylindrical and has an outer diameter no greater than 3 mm.

3. The device of claim 1, wherein the multiple articulable links comprise a first articulable intermediate link pivotally connected to the elongated proximal tube, a second articulable intermediate link pivotally connected to the first articulable intermediate link, and an articulable end link pivotally connected to the second articulable intermediate link.

4. The device of claim 1, wherein adjacent articulable links are configured to pivot in different orthogonal planes.

5. The device of claim 1, wherein the sensor further includes a flexible sensor beam having one or more sensor elements attached thereto, wherein the sensor head flexes the sensor beam when the sensor head is pressed against tissue.

6. The device of claim 5, wherein the sensor head includes a proximally facing protrusion that contacts a central portion of the flexible sensor beam.

7. The device of claim 5, wherein the one or more sensor elements comprise one or more strain gauges.

8. The device of claim 5, wherein the sensor further includes a sensor body having opposed ledges that each support an end of the flexible sensor beam and a beam clamp that securely clamps the ends of the flexible sensor beam against the ledges.

* * * * *